United States Patent
Poka et al.

[11] Patent Number: 6,162,222
[45] Date of Patent: Dec. 19, 2000

[54] METHOD AND APPARATUS FOR EXTERNAL FIXATION OF THE PELVIS

[75] Inventors: Attila Poka, Columbus, Ohio; Kirk J. Bailey, Andover, N.J.; Rui J. Ferreira, Newark, N.J.; John Scott Mahaffey, Hackettstown, N.J.

[73] Assignee: Electro Biology, Inc., Parsippany, N.J.

[21] Appl. No.: 09/189,876

[22] Filed: Nov. 11, 1998

[51] Int. Cl.[7] .................................................. A61B 17/60
[52] U.S. Cl. .................................. 606/54; 606/57; 606/59
[58] Field of Search .................................. 606/54, 55, 57, 606/58, 59

[56] References Cited

U.S. PATENT DOCUMENTS

| | | | |
|---|---|---|---|
| 4,292,964 | 10/1981 | Ulrich | 128/92 EB |
| 4,361,144 | 11/1982 | Slätis et al. | 128/92 A |
| 4,815,455 | 3/1989 | Kim | 182/92 Z |
| 4,957,495 | 9/1990 | Kluger | 606/58 |
| 5,108,397 | 4/1992 | White | 606/60 |
| 5,196,012 | 3/1993 | Malka | 606/54 |
| 5,350,378 | 9/1994 | Cole et al. | 606/57 |
| 5,620,442 | 4/1997 | Bailey et al. | 606/54 |
| 5,676,664 | 10/1997 | Allard et al. | 606/57 |

FOREIGN PATENT DOCUMENTS

WO 97/35527  10/1997  WIPO.

*Primary Examiner*—Michael Buiz
*Assistant Examiner*—Julian W. Woo
*Attorney, Agent, or Firm*—Harness, Dickey & Pierce, P.L.C.

[57] ABSTRACT

An apparatus for external fixation of the pelvis includes first and second pluralities of bone screws adapted to be connected to first and second portions of the pelvis, respectively. The apparatus additionally includes a first bone screw clamp for receiving the first plurality of bone screws and a second bone screw clamp for receiving the second plurality of bone screws. Further, the apparatus includes a frame for securing the first bone screw clamp to the second bone screw clamp. The frame includes a transversely extending member which is articulable between a first position and a second position such that the transversely extending member is displaced in an inferior/superior direction when the frame is articulated from the first position to the second position.

20 Claims, 5 Drawing Sheets

METHOD AND APPARATUS FOR EXTERNAL FIXATION OF THE PELVIS

BACKGROUND OF THE INVENTION

1. Field of the Invention

The present invention relates generally to the external fixation of bones. More particularly, the present invention relates to a method and apparatus for external fixation of the pelvis. While not limited thereto, the present invention specifically relates to an apparatus for external pelvic fixation which is applied anteriorly and provides enhanced surgical access to the abdominal area.

2. Discussion of the Related Art

In various orthopedic surgical procedures, it is necessary to secure two bone portions in a relatively fixed relationship to each other. For example, the need for establishing such a secured relationship is often a result of a fracture which has occurred to the bone. To ensure that the bone can regenerate in the proper orientation and fuse the fracture, it is important that the bone portions be accurately aligned and the relative positions maintained for an extended time period.

Various external fixation devices for the repair of traumatized bone are known. For example, commonly assigned U.S. Pat. No. 5,662,650 to Bailey et al. discloses an apparatus for the external fixation of large bones. The apparatus is illustrated to generally include a main body as well as a first and second bone screw clamps. The main body serves to allow the apparatus to axially rotate, thereby providing a proper longitudinal rotational location of the bone screws with respect to a bone. The first bone screw clamp is used to secure a first bone screw to the apparatus while permitting the first bone screw to be axially displaced from the main body. In a similar fashion, the second bone screw clamp functions to secure a second bone screw to the apparatus and to allow the second bone screw to be axially displaced with respect to the main body. U.S. Pat. No. 5,662,650 is incorporated by reference as if fully set forth herein.

In certain orthopedic surgical procedures, it is necessary to externally fixate portions of the pelvis relative to each other. The need for such external fixation is typically the result of a fracture. The pelvis normally functions to support a number of organs in a compact area. When the pelvis fractures (e.g. posterior disruption or anterior disruption), the patient's life may depend on quick closure and stabilization of the pelvis. Other injuries requiring surgical repair may be present due to the nature of the typical accidents resulting in pelvic fractures.

One known device available for pelvic external fixation is shown and described in U.S. Pat. No. 5,350,378. The device includes a frame, first and second fixation bone screws connected to the frame in spaced relationship to each other, an adjustment mechanism for moving the first and second fixation bone screws relative to each other, and an adjustable spacer for adjusting distance between the device and the patient. The disclosed device is specifically intended to be engaged with the pelvis in an posterior fashion.

While known external fixation devices specifically designed for the pelvis, including but not limited to the type disclosed in U.S. Pat. No. 5,350,378, may have proven acceptable for certain applications, such fixators are nevertheless susceptible to improvements that may enhance their performance. For example, many known devices for external fixation of the pelvis must be applied in a posterior fashion (i.e., with a frame passing behind the patient.) Posterior application forces the patient to lie on his or her stomach resulting in additional patient discomfort. In addition, posterior application impedes medical access to the patient's abdomen. Fractures of the pelvis often occur from traffic accidents, free falls, and industrial accidents associated with other severe injuries, often to the abdominal area. Insofar as the present invention is concerned, known devices adapted for anterior application do not provide sufficient surgical access to the patient, particularly in the abdominal area. Furthermore, known devices do not permit independent pin placement allowing for quick installation of pins into the iliac crest.

SUMMARY OF THE PRESENT INVENTION

The external fixator of the present invention includes means for receiving a first bone screw secured to a first portion of a pelvis, and means for receiving a second bone screw secured to a second portion of the pelvis. The external fixator additionally includes a frame securing the means for receiving the first bone screw to the means for receiving the second bone screw. The frame includes a transversely extending member movable in an inferior/superior direction between first and second positions which selectively provides surgical access to the abdomen of a patient.

In one form, the present invention provides an apparatus for external fixation of a pelvis which includes first and second pluralities of bone screws adapted to be connected to first and second portions of the pelvis, respectively. The apparatus additionally includes a first bone screw clamp for receiving the first plurality of bone screws and a second bone screw clamp for receiving the second plurality of bone screws. Further, the apparatus of the present invention includes a frame for securing the first bone screw clamp to the second bone screw clamp. The frame includes a transversely extending member and is articulable between a first position and a second position such that the transversely extending member is displaced in an inferior/superior direction when the frame is articulated from the first position to the second position.

In another form, the present invention provides a method for securing a first portion of a pelvis to a second portion of the pelvis. The method includes the general steps of forming a first bone screw clamp and forming a second bone screw clamp. The method additionally includes the general steps of connecting the first plurality of bone screws to the first bone screw clamp and connecting the second plurality of bone screws to the second bone screw clamp. Further, the method of the present invention includes the general step of interconnecting the first bone screw clamp and the second bone screw clamp through a frame. The frame includes a transversely extending member adapted to be positioned anterior to the pelvis. In another general step of the present invention, the frame is articulated such that the transversely extending member is displaced in an inferior/superior direction between a first position and a second position.

An advantage of the present invention is the provision of a method and apparatus for external pelvic fixation which is applied in an anterior fashion.

Another advantage of the present invention is the provision of a method and apparatus for external pelvic fixation which allows for sufficient surgical access to the abdominal area when the apparatus is applied anteriorly.

Another advantage of the present invention is the provision of a method and apparatus for external pelvic fixation which allows for the placement of converging bone screws into the iliac crest of the pelvis to obtain secure fixation.

A related advantage of the present invention is the provision of a method and apparatus for external pelvic fixation which allows freedom of bone screws in three planes.

Additional advantages and features of the present invention will become apparent from the following description and appended claims, taken in conjunction with the accompanying drawings.

BRIEF DESCRIPTION OF THE DRAWINGS

FIG. 5 is an illustration of a second telescopic member shown in FIGS. 1 and 2 according to the teachings of the preferred embodiment of the present invention operatively associated with a cross-bar.

DETAILED DESCRIPTION OF THE PREFERRED EMBODIMENT

Figure 1:
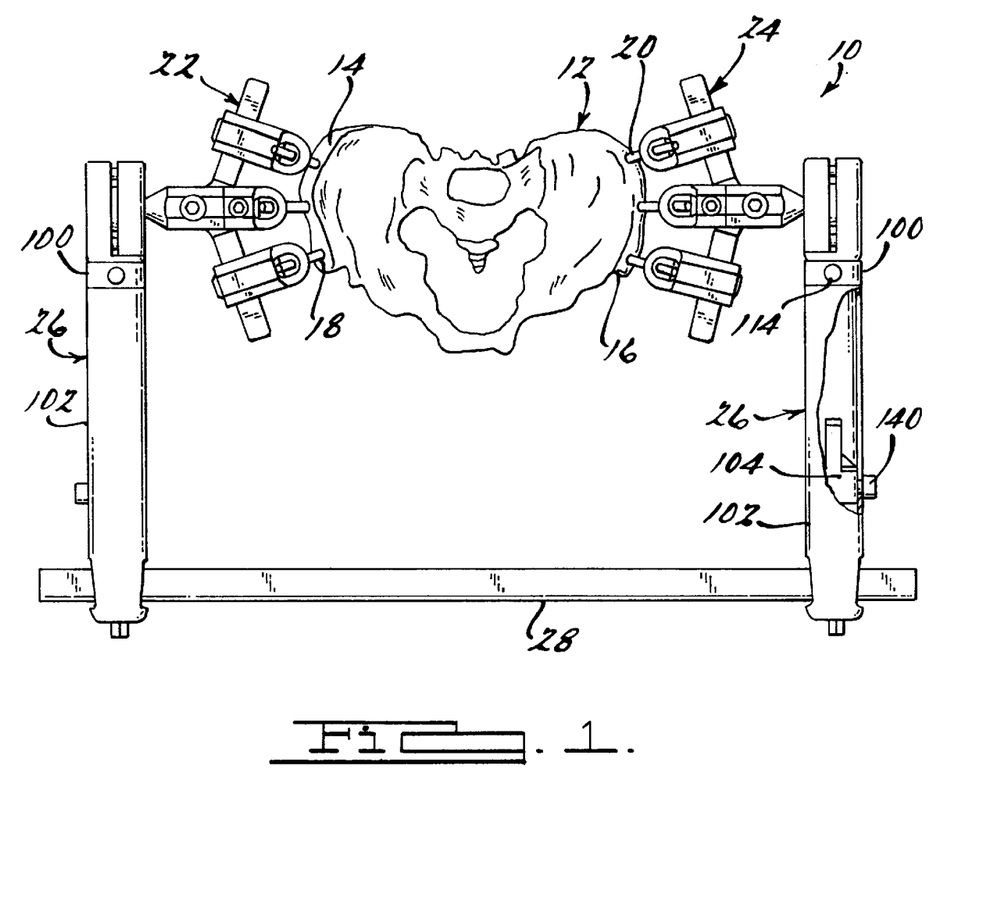
FIG. 1 is a superior view of a portion of the pelvis operatively associated with an apparatus for external fixation of the pelvis according to the teachings of the preferred embodiment of the present invention.

Referring initially to FIG. 1, an apparatus constructed in accordance with the teachings of a preferred embodiment of the present invention is generally identified with reference numeral 10. The apparatus 10 is illustrated in an exemplary use environment operatively associated with a human pelvis 12. The following description of the preferred embodiment of the present invention is merely exemplary in nature and is in no way intended to limit the invention or its application or uses. In this regard, it will be understood that the teachings of the present invention have application for the fixation of bones other than the pelvis 12.

The apparatus 10 is shown connected to a first portion 14 and a second portion 16 of the pelvis 12. Preferably, the apparatus 10 is connected to the iliac crest adjacent one medial/lateral side of the pelvis 12 through a first plurality of bone screws 18 and to the iliac crest adjacent the other medial/lateral side of the pelvis 12 through a second plurality of bone screw 20. As will become more apparent below, the apparatus 10 of the present invention permits the first and second pluralities of bone screws 18 and 20 to convergingly engage the respective portions 14 and 16 of the iliac crest to thereby obtain secure fixation.

Figures 2, 3, 4, 6:
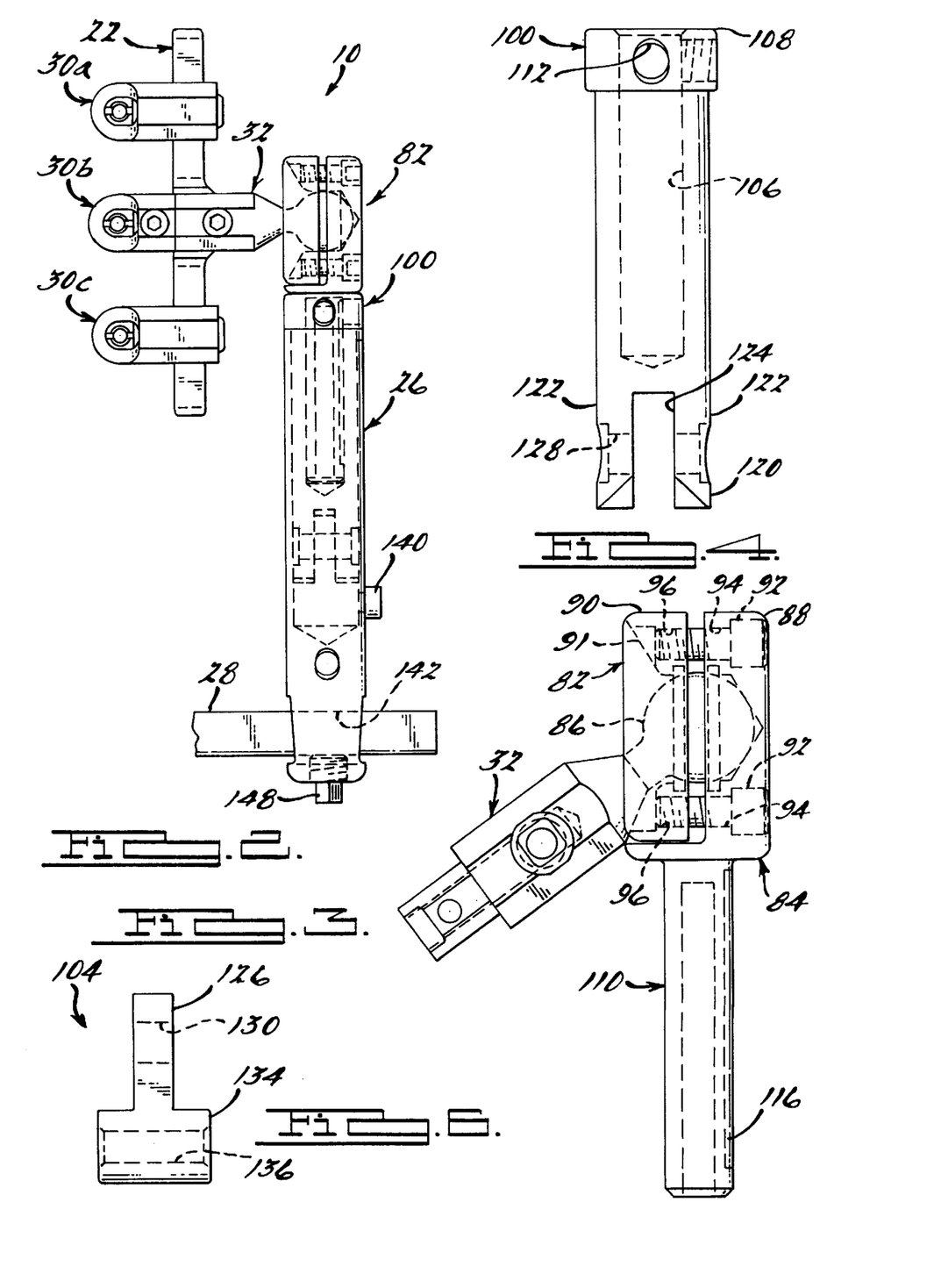
FIG. 2 is an enlarged view illustrating a portion of the apparatus for external fixation of the pelvis according to the teachings of the preferred embodiment of the present invention.
FIG. 3 is an illustration of one of the bone screw clamp assemblies and an associated rail member shown in FIGS. 1 and 2 according to the teachings of the preferred embodiment of the present invention.
FIG. 4 is an illustration of a first telescopic member shown in FIGS. 1 and 2 according to the teachings of the preferred embodiment of the present invention.
FIG. 6 is an illustration of a connector knuckle shown in FIGS. 1 and 2 according to the teachings of the preferred embodiment of the present invention.
Figure 6:
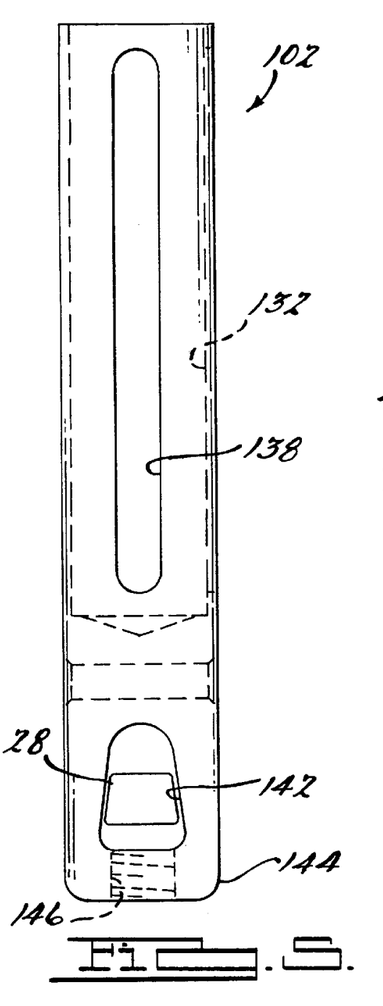

With continued reference to FIG. 1 and additional reference to FIG. 2, the apparatus 10 of the present invention is shown to generally include first and second bone screw clamping assemblies 22 and 24 for adjustably receiving the first and second pluralities of bone screws 18 and 20, respectively. The apparatus 10 is additionally shown to generally include a pair of telescopic tower assemblies 26 and a transversely extending member or cross-bar 28. Each of the tower assemblies 26 is operative to interconnect an associated one of the first and second bone screw clamping assembly 22 and 24 to the crossbar 28. In the preferred embodiment, the cross-bar 28 is constructed from a radiolucent material. It will be understood that the bone screw clamping assemblies 22 and 24 are substantially identical and that the pair of telescopic tower assemblies 26 are also substantially identical. Further in this regard, it will be understood that the apparatus 10 is a substantially mirror image about a medial/lateral centerline.

Figure 7:
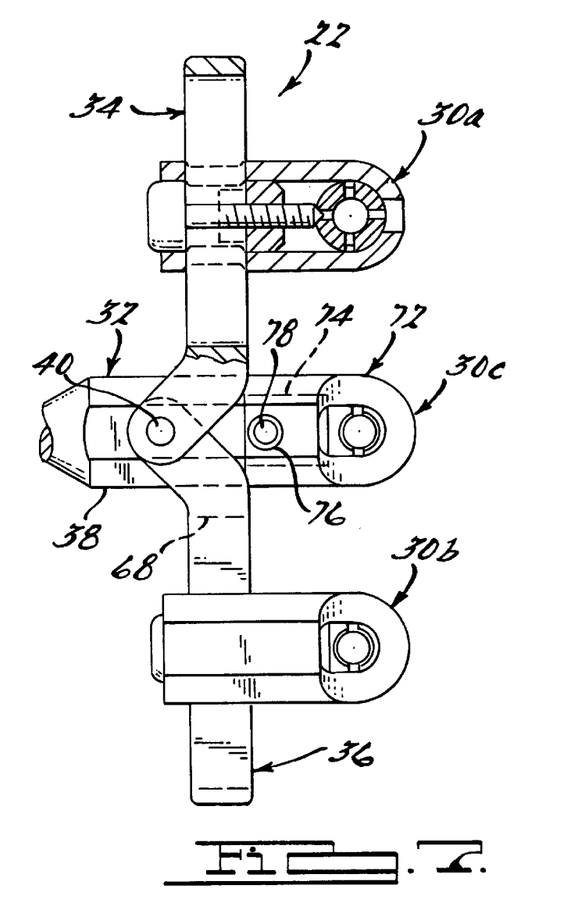
FIG. 7 is a partially cut-away view of one of the bone screw clamp assemblies shown in FIGS. 1 and 2 according to the teachings of the preferred embodiment of the present invention.

The first bone screw clamping assembly 22 will be described in detail with continued reference to FIGS. 1 and 2 and additional reference to FIGS. 7 and 8. The bone screw clamping assembly 22 is shown to generally include a plurality of bone screw clamping units 30a, 30b, and 30c carried by a base 32. In the particular embodiment illustrated, outer bone screw clamping units 30a and 30b are identical in construction and are movably carried on first and second arms 34 and 36, respectively. The first and second arms 34 and 36 are both pivotally attached to an intermediate portion 38 of the base 32 by a fastener 40. The fastener 40 defines a pivot axis about which the first and second arms 34 and 36 may rotate prior to tightening thereof.

Figure 8:
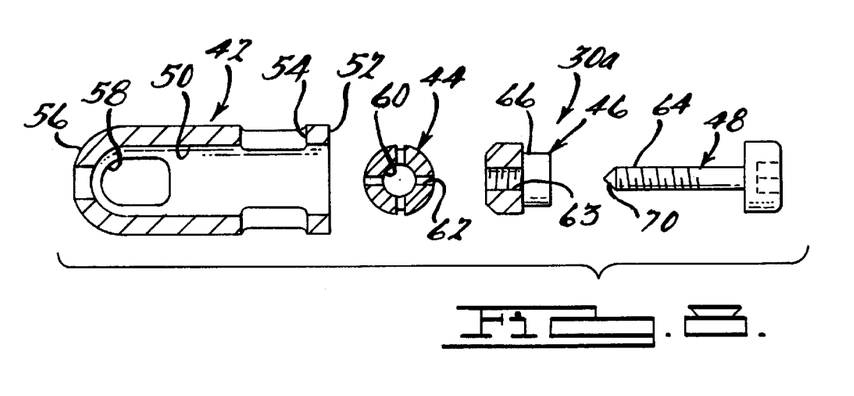
FIG. 8 is an exploded and partially cut-away view of one of the bone screw clamps of FIG. 8.

As shown specifically in FIG. 8, the bone screw clamping unit 30a includes a main body portion 42, a bone screw receiving portion 44, a clamping element 46, and a threaded fastener 48. The main body portion 42 is hollow and defines an elongated channel 50. Adjacent a first end 52 at which the elongated channel 50 opens, the main body portion 42 includes an aperture 54 for slidably receiving the arm 34. Adjacent the other end 56 of the main body portion 42, provided is an aperture 58 for receiving one of the first plurality of bone screws 18.

The bone screw receiving portion 44 of the bone screw clamping unit 30a is spherical in shape and includes an aperture 60 passing therethrough for directly receiving one of the first plurality of bone screws 18. The bone screw receiving portion 44 is further shown to include a plurality of compression slots 62 which intersect the aperture 60 and are oriented parallel to the aperture 60. The bone screw receiving portion 44 is inserted into the main body portion 42 through the open end 52 and oriented so that the aperture 60 is substantially aligned with the opening 58 for receiving one of the bone screws 18.

The clamping element 46 is generally cylindrical in shape and has an external diameter slightly smaller than the internal diameter of the elongated channel 50. The clamping element 46 defines a threaded aperture 63 for receiving an externally threaded shank 64 of the threaded fastener 48. The clamping element 46 further includes a pair of legs 66 (one of which is shown in the cross-sectional view of FIG. 8) spaced apart to receive the arm 34. The fastener 48 is adapted to pass through an elongated slot 68 provided in the arm 34 while the legs 66 are positioned on either side of the arm 34. Rotation of the threaded fastener 48 functions to draw the clamping element 46 against the arm 34 and thereby fix the location of the bone screw clamping unit 30a relative to the arm 34. Rotation of the threaded fastener 48 further serves to secure the bone screw 18 within the bone screw receiving portion 44. In this regard, rotation of the threaded fastener 48 causes a distal tip 70 of the threaded fastener 48 to advanced towards the bone screw receiving portion 44, causing the bone screw receiving portion 44 to slightly compress. The screw receiving portions 44 allow movement of the bone screws 18 in three places. By providing this freedom, a surgeon can place the bone screws 18 in a converging fashion into the iliac crest 14.

The intermediate clamping unit 30c is similar in construction to the outer clamping units 30a and 30b in that it includes a similar but shortened main body portion 72 and an identical bone screw receiving portion 44. An upper end 74 (shown in phantom in FIG. 7) of the base 32 is telescopically received by the channel 50 defined by the main body portion 72. An aperture 76 is provided in the main body portion 72 for receiving a threaded fastener 78 for engaging a threaded aperture (not specifically shown) provided in the upwardly extending portion 74. Upon tightening the fastener 78, the main body portion 72 of the intermediate bone screw clamping unit 30c is drawn downwardly causing the main body portion 72 to compress the bone screw receiving portion 44 against the upwardly extending portion 74. This action secures the bone screw 18 to the bone screw clamping unit 30c and also fixes the orientation of the bone screw 18.

To provide means for universal movement between the telescopic tower assemblies 26 and the associated bone screw clamping assemblies 22 and 24, the present invention includes a pair of rail members 82. With specific reference to FIG. 3, each of the pair of telescopically tower assemblies 26 is illustrated to include a rail member 82 for adjustably receiving an associated one of the first and second bone screw clamp assemblies 22 and 24. The rail members 82 are shown to include a clamping portion 84 for receiving a spherical end 86 carried by the base 32 of the bone screw clamping assembly 22. As will become apparent, the clamping portion 84 and the spherical end 86 allow for universal movement between the bone screw clamping assembly 22 and the associated one of the telescopic tower assemblies 26.

The clamping portion 84 of the rail member 82 includes a base 88 and a cover 90. The base 88 is connected to the cover 90 through a pair of threaded fasteners 92 which pass through apertures 94 provided in the base and engage threaded apertures 96 provided in the cover 90. The spherical end 86 of the base 32 is rotatably captured between the base 88 and the cover 90. The cover 90 defines an aperture 91 with tapering sidewalls. In the preferred embodiment, the tapering sidewalls allow the associated bone clamping assembly 22 to angulate a total of approximately 72 degrees in any direction. Tightening of the fasteners 92 serves to clamp the spherical end 86 between the base 88 and the cover 90, thereby arresting relative movement between the bone screw clamp assembly 22 and the rail member 82.

To provide means for articulating the cross-bar 28 between first and second positions, each of the telescopic tower assemblies 26 is further shown to generally include first and second telescoping members 100 and 102 pivotally interconnected by a translatable knuckle 104. As shown specifically in FIG. 4, the first telescoping member 100 defines an elongated channel 106 open adjacent an enlarged first end 108 of the first telescoping member 100. The elongated channel 106 is generally circular in cross-section with a diameter sized to slidably receive a male extension 110 integrally formed with the base 88 of the rail member 84. The enlarged first end 108 of the first telescoping member 100 is formed to include one or more radially extending apertures 112 which are internally threaded and intersect the elongated channel 106. The apertures 112 are adapted to receive a locking screw 114 which engages a groove 116 provided in the male extension 110. Upon tightening of the locking screw 114, rotational and translational movement of the male extension 110 relative to the first telescoping member 100 is arrested. The telescopic relationship between the rail member 82 and the first telescoping member 100 provides for adjustment of the frame's height to best fit the patient's size.

With continued reference to FIG. 4 and additional reference to FIG. 6, a second end 120 of the first telescoping member 100 includes a pair of spaced apart flanges 122 which define an opening 124. The opening 124 is adapted to receive a male flange 126 carried by the knuckle 104. Aligning apertures 128 and 130 are provided in the flanges 122 and 126, respectively, for receiving a fastener 131 (shown in FIGS. 9C–9D). The fastener 131 defines a pivot axis.

With continued reference to FIG. 6 and additional reference to FIG. 5, the second telescoping member 102 is shown to define an elongated cylindrical channel 132 for slidably receiving the first telescoping member 100 and the knuckle 104. The knuckle 104 includes a cylindrical end 134 formed to include an internally threaded aperture 136 passing therethrough. The internally threaded aperture 136 is adapted to align with an elongated slot 138 provided in the second telescoping member 102. A threaded fastener 140 (shown in FIG. 1) passes through the elongated slot 138 and engages the internally threaded aperture 136. Upon tightening of the fastener 140, telescopic movement between the first and second telescoping members 100 and 102 is arrested.

The second telescoping member 102 is further formed to include an aperture 142 for receiving the cross-bar 28. The aperture 142 is shown in FIG. 5 to taper in a direction away from an adjacent end 144 of the second telescoping member 102. In the preferred embodiment, the cross-bar 28 has a pair of tapering sides. The adjacent end 144 of the second telescoping member 102 is further formed to include a threaded aperture 146 intersecting the aperture 142. The threaded aperture 146 receives a clamping member 148 adapted to arrest relative movement between the second telescoping member and the cross-bar 28 upon tightening by forcing the cross-bar 28 away from the end 144.

Figure 9A:
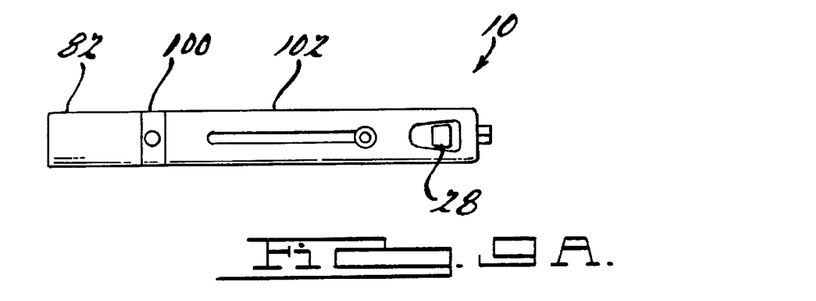
FIGS. 9A–9D represent a series of simplified side views of the apparatus according to the teachings of a preferred embodiment of the present invention shown articulated from a first position to a second position.
Figure 9B:
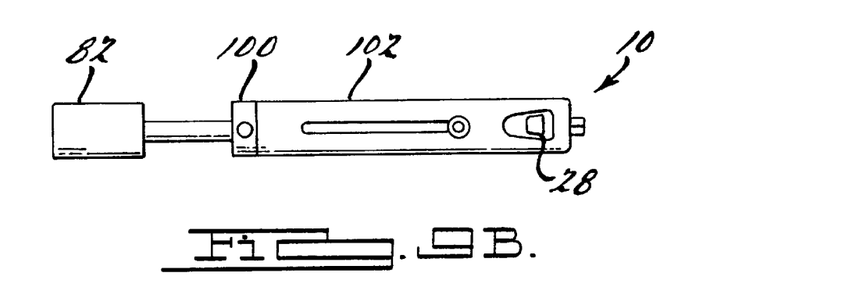
Figure 9C:
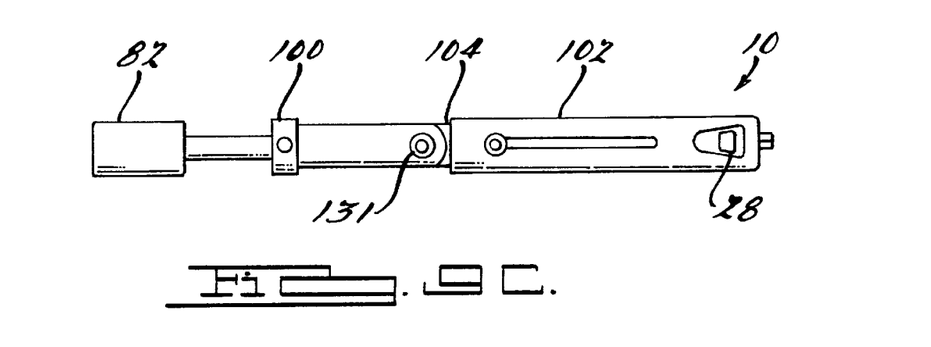

Operation of the apparatus 10 of the present invention will be further described with continued reference to FIG. 1 and additional reference to FIGS. 9A–9D. As noted above, the telescopic tower assemblies 26 permit the cross-bar 28 to be articulated between first and second positions. In accordance with the teachings of the preferred embodiment of the present invention, the cross-bar 28 is intended to be positioned anterior to the pelvis and transverse the patient's abdomen. In the first position, which is shown in FIGS. 1 and 9A, the first telescoping portion member 100 is telescopically retracted within the second telescoping member 102 and the rail member 82 is retracted within the first telescoping member 100. The rail member 82 may be extended from the first telescoping member 100, as shown in FIG. 9B, to accommodate patients of various sizes.

Figure 9D:
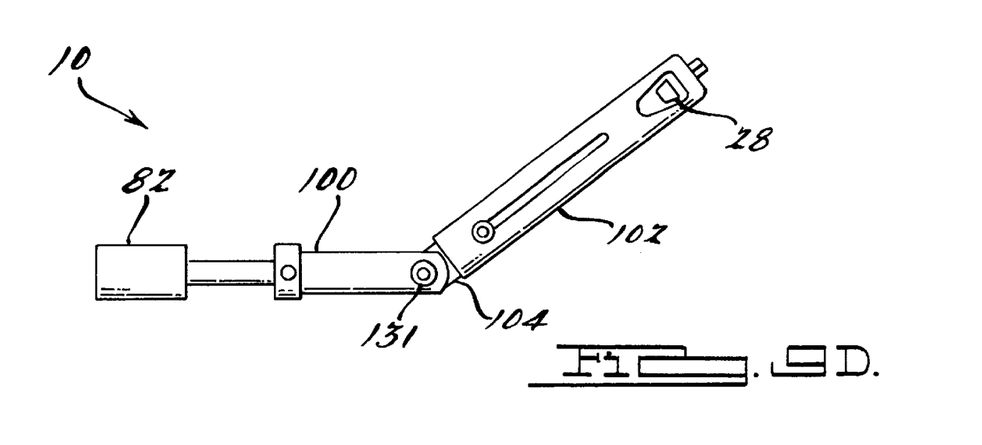

In order to articulate the cross-bar 28 to the second position (shown in FIG. 9D), the cross-bar 28 is first translated to an intermediate position (shown in FIG. 9C) through telescopic extension of the first telescoping member 100 relative to the second telescoping member 102. Upon complete extension, the second end 120 of the first telescoping member 100 extends beyond the second telescoping member 102, thereby exposing the pivot axis between the first and second telescoping portions 100 and 102. In this intermediate position, the cross-bar 28 can be pivotally articulated about the pivot axis defined by the fastener interconnecting the first telescoping member 100 and the knuckle 104. Once pivoted to the second position, the cross-bar 28 is displaced in an inferior/superior direction relative to the first position, thereby providing surgical access to the patient's abdomen. As shown in FIG. 9D, the cross-bar 28 is displaced superiorly. Alternatively, it will be understood that the cross-bar 28 may be displaced inferiorly.

Figure 10:
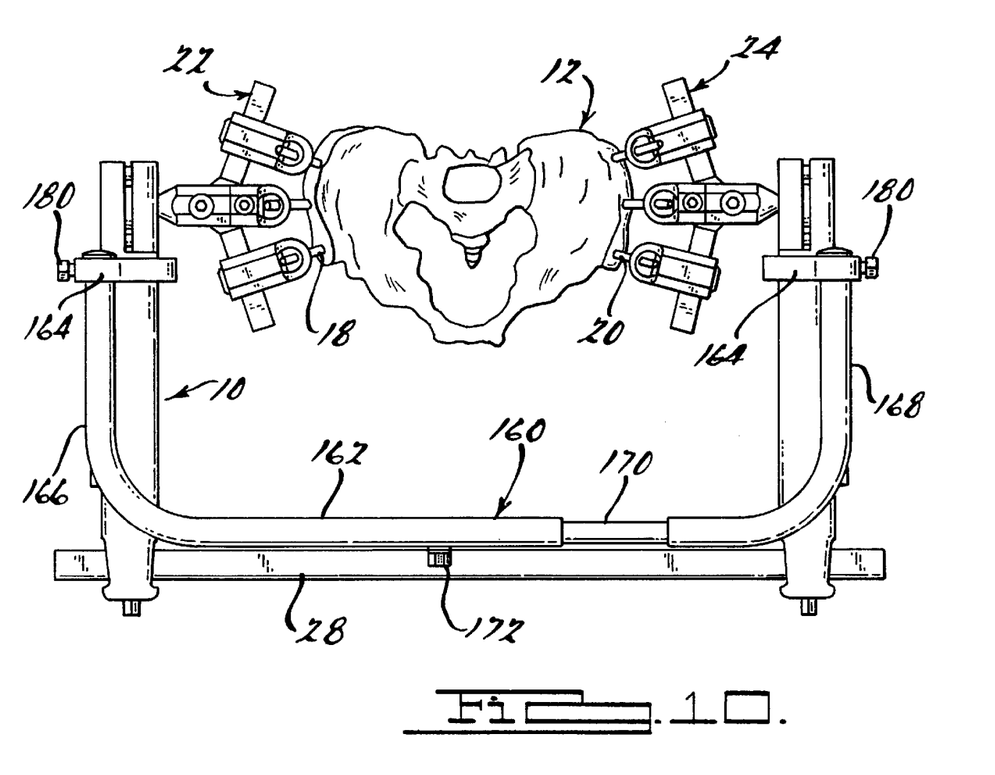
FIG. 10 is a view similar to FIG. 1 further illustrating a brace of the present invention for maintaining the relative positions of the bone screw clamp assemblies as the fixator is articulated.
Figure 11:
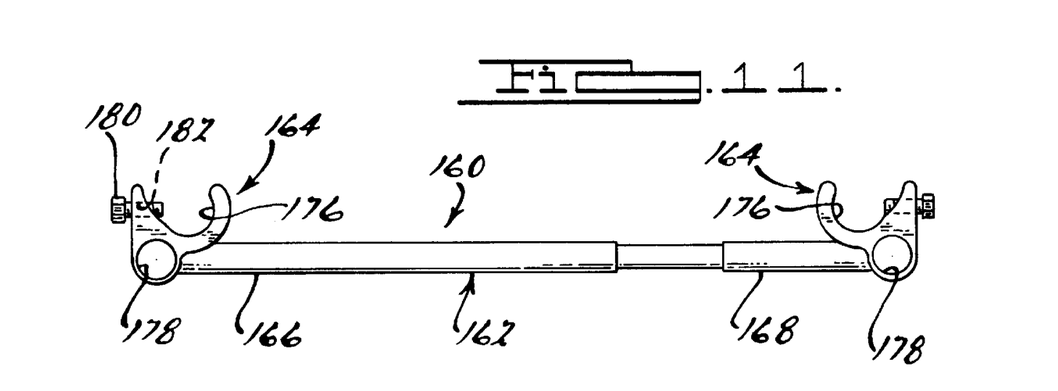
FIG. 11 is a front view of the brace of FIG. 10.

With reference to FIGS. 10 and 11, the present invention is further shown to include a brace 160 for maintaining the relative positions of the first and second pluralities of bone screws 18 and 20 as the apparatus 10 is articulated. It will become apparent below that the brace 160 provides a rigid interconnection between the first and second pluralities of bone screws 18 and 20 such that the pelvis 12 may be stabilized while the apparatus 10 is adjusted. The brace 160 is intended to be removably attached to the apparatus 10 as required, and then subsequently removed following articulation of the apparatus 10.

The apparatus 10 is illustrated to generally include a U-shaped frame portion 162 and first and second connection members 164. In the exemplary embodiment illustrated, the frame portion 162 includes first and second L-shaped segments 166 and 168 constructed of hollow, cylindrical steel. An intermediate steel rod 170 adjustably connects the first and second L-shaped segments 166 and 168. To provide such adjustability, a first end of the rod 170 is inserted into the first L-shaped segment 166 and welded, press-fit or otherwise suitably attached thereto. A second end of the rod 170 is telescopically received within the second L-shaped segment 168.

To provide means for locking the brace 160 at a desired width, a threaded fastener 172 is provided. The threaded fastener 172 passes through an elongated slot (not shown) provided in the second L-shaped segment 168 and engages a threaded aperture (not shown) provided in the rod 170. Clockwise rotation of the fastener functions to arrest relative movement between the second L-shaped segment 168 and the rod 172.

The first and second connection members 164, which will be understood to be substantially identical in construction and function, serve to interconnect the frame portion 162 of the brace 160 to the apparatus 10. As illustrated, each of the connection members 164 partially defines an arcuate channel 176 for receiving an associated one of the first telescoping members 100. In addition, each of the connection members 164 includes an aperture 178 which receives an associated one of the first and second L-shaped segments 166 and 168. A threaded fastener 180 passes through an aperture 182 provided in the connection member 164. The threaded fastener 180 is adapted to engage one of the apertures 112 provided in the associated first telescoping member 100.

When the brace 160 is operatively installed, as shown in FIG. 10, the apparatus 10 can be articulated without disturbing the stabilization of the pelvis 12. For example, if the brace 160 were absent telescoping of the apparatus 10 between the first position (shown in FIG. 9A) and the intermediate position (shown in FIG. 9C) would result in an anterior/posterior sheer force applied to the pelvis 12. The brace 160, however, allows for equal sliding of the telescoping members.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments following within the description of the appended claims.

What is claimed is:

1. An apparatus for external fixation of a pelvis, the apparatus comprising:

a first plurality of bone screws adapted to convergingly engage said first bone portion, said first plurality of bone screws including a first bone screw;

a second plurality of bone screws adapted to convergingly engage said second bone portion, said second plurality of bone screws including a second bone screw;

means for receiving said first plurality of bone screws;

means for receiving said second plurality of bone screws; and a frame securing said means for receiving said first plurality of bone screws to said means for receiving said second plurality of bone screws, said frame including an elongated member movable in between first and second positions a generally transverse to a plane between said means for receiving said first plurality of bone screws and said means for receiving said second plurality of bone screws.

2. The apparatus for external fixation of a pelvis of claim 1, wherein the apparatus is adapted to attach to the pelvis anteriorly.

3. The apparatus for external fixation of a pelvis of claim 1, wherein said elongated member is linearly displaceable in a direction along an axis parallel to the elongated member.

4. The apparatus for external fixation of a pelvis of claim 3, further comprising means for selectively locking said frame in both of said first and second positions.

5. An apparatus for external fixation of a pelvis of claim 1, wherein said elongated member is pivotable about a pivot axis parallel to said elongated member.

6. An apparatus for external fixation of a pelvis, the apparatus comprising:

a first plurality of bone screws adapted to be connected to a first portion of the pelvis;

a second plurality of bone screws adapted to be connected to a second portion of the pelvis;

a first bone screw clamp for receiving the first plurality of bone screws;

a second bone screw clamp for receiving the second plurality of bone screws;

a frame for securing said first bone screw clamp to said second bone screw clamp, said frame including an elongated member, said frame articulable between a first position and a second position such that said elongated member is displaced in a direction generally transverse to a plane between said first bone screw clamp and said second bone screw clamp.

7. The apparatus for external fixation of a pelvis of claim 6, wherein the apparatus is adapted to attach to the pelvis anteriorly.

8. The apparatus for external fixation of a pelvis of claim 7, wherein said elongated member is linearly displaceable in an anterior direction relative to said first and second pluralities of bone screws.

9. The apparatus for external fixation of a pelvis of claim 8, wherein said first plurality of bone screws converge and wherein said second plurality of bone screws converge.

10. The apparatus for external fixation of a pelvis of claim 7, further comprising means for selectively locking said frame in both of said first and second positions.

11. The apparatus for external fixation of a pelvis of claim 8, wherein said elongated member is pivotable about a pivot axis parallel to said elongated member.

12. An apparatus for external fixation of a pelvis, the apparatus comprising:
    a first plurality of bone screws adapted to be connected to a first portion of the pelvis;
    a second plurality of bone screws adapted to be connected to a second portion of the pelvis;
    a first bone screw clamp for receiving said first plurality of bone screws such that the bone screws of said first plurality of bone screws are free to move in three planes;
    a second bone screw clamp for receiving said second plurality of bone screws; and
    a frame for securing said first bone screw clamp to said second bone screw, said frame including an elongated member telescopically interconnected to said first and second bone screw clamps, said elongated member movable between a first position whereat the elongated member is positioned anterior to the pelvis and a second position whereat said elongated member is positioned anterior to the pelvis and displaced in from said first position.

13. The apparatus for external fixation of a pelvis of claim 12, wherein said first plurality of bone screws converge and wherein said second plurality of bone screws converge.

14. The apparatus for external fixation of a pelvis of claim 12, wherein said elongated member is movable between said first and second positions such that said elongated member linearly translates from said first position in a direction transverse to its longitudinal axis to an intermediate position and said elongated member rotates about a pivot axis parallel to its longitudinal direction from said intermediate position to said second position.

15. An apparatus for external fixation of a pelvis of claim 13, further comprising means for selectively locking said transversely extending member in both of said first and second positions.

16. An apparatus for external fixation of a pelvis, the apparatus comprising:
    a first plurality of bone screws adapted to be connected to a first portion of the pelvis;
    a second plurality of bone screws adapted to be connected to a second portion of the pelvis;
    a first bone screw clamp for receiving the first plurality of bone screws;
    a second bone screw clamp for receiving the second plurality of bone screws;
    a frame for securing said first bone screw clamp to said second bone screw clamp, said frame including an elongated member and first and second telescoping assemblies, first and second telescoping assemblies connecting said elongated member and said first and second bone screw clamps, respectively, said frame articulable between a first position and a second position such that said elongated member is displaced in a direction transverse to the longitudinal axes of said first and second telescoping assemblies when said frame is articulated from said first position to said second position.

17. The apparatus for external fixation of a pelvis of claim 16, wherein said first and second telescoping assemblies each include first and second telescopic members pivotally connected by a translatable knuckle.

18. The apparatus for external fixation of a pelvis of claim 16, wherein both of said first and second telescoping assemblies include a rail assembly for adjustably receiving an associated one of the first and second bone screw clamps.

19. The apparatus for external fixation of a pelvis of claim 16, wherein said first and second bone screw clamps include a spherical end and wherein said rail assemblies each have a clamping portion for receiving said spherical of one of said first and second bone screw clamps.

20. The apparatus for external fixation of a pelvis of claim 16, further comprising a brace for maintaining a relative position between said first and second bone screw clamps as said frame is articulated between said first and second positions.

* * * * *

UNITED STATES PATENT AND TRADEMARK OFFICE
CERTIFICATE OF CORRECTION

PATENT NO. : 6,162,222  
DATED : December 19, 2000  
INVENTOR(S) : Attila Poka et al.

Page 1 of 1

It is certified that error appears in the above-identified patent and that said Letters Patent is hereby corrected as shown below:

Column 1,  
Line 28, delete "a".  
Line 58, "an" should be -- a --.

Column 5,  
Line 8, "advanced" should be -- advance --.

Column 8,  
Line 32, delete "a" and insert -- in a direction --.

Column 9,  
Line 6, "claim 8" should be -- claim 7 --.  
Line 34, delete "in".  
Line 45, "direction" should be -- axis --.

Column 10,  
Line 38, after "spherical" insert -- end --.

Signed and Sealed this

First Day of April, 2003

JAMES E. ROGAN  
*Director of the United States Patent and Trademark Office*